United States Patent
Wagenaar Cacciola et al.

(10) Patent No.: US 9,463,333 B2
(45) Date of Patent: Oct. 11, 2016

(54) SKIN TREATMENT DEVICE, LAMP AND USE

(75) Inventors: Giovanna Wagenaar Cacciola, Eindhoven (NL); Yvonne Elizabeth Dietzenbacher-Jansen, Eindhoven (NL); Adriaantje Pieternella Mouws-Van Rossum, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1043 days.

(21) Appl. No.: 12/667,242

(22) PCT Filed: Sep. 17, 2007

(86) PCT No.: PCT/IB2007/053737
§ 371 (c)(1),
(2), (4) Date: Dec. 30, 2009

(87) PCT Pub. No.: WO2009/004412
PCT Pub. Date: Jan. 8, 2009

(65) Prior Publication Data
US 2010/0179622 A1 Jul. 15, 2010

(30) Foreign Application Priority Data
Jul. 5, 2007 (EP) .................................. 07111846

(51) Int. Cl.
*A61N 5/06* (2006.01)

(52) U.S. Cl.
CPC .......... *A61N 5/0614* (2013.01); *A61N 5/0616* (2013.01); *A61N 2005/0615* (2013.01); *A61N 2005/0642* (2013.01); *A61N 2005/0652* (2013.01); *A61N 2005/0655* (2013.01); *A61N 2005/0661* (2013.01); *A61N 2005/0662* (2013.01)

(58) Field of Classification Search
CPC ...................................... A61N 5/0614–5/0616
See application file for complete search history.

(56) References Cited

U.S. PATENT DOCUMENTS

| | | | | |
|---|---|---|---|---|
| 4,243,906 A | * | 1/1981 | Wilson | 313/623 |
| 4,524,299 A | | 6/1985 | Preston, III | |
| 5,892,619 A | * | 4/1999 | Chubb et al. | 359/361 |
| 6,157,141 A | | 12/2000 | Lapatovich et al. | |
| 2004/0034397 A1 | | 2/2004 | Lin | |
| 2004/0056600 A1 | * | 3/2004 | Lapatovich et al. | 313/634 |
| 2004/0176823 A1 | * | 9/2004 | Island et al. | 607/88 |
| 2004/0232359 A1 | | 11/2004 | Fiset | |
| 2005/0085877 A1 | * | 4/2005 | Kratz | 607/94 |

(Continued)

FOREIGN PATENT DOCUMENTS

| | | |
|---|---|---|
| DE | 4026327 A1 | 2/1992 |
| FR | 2342745 A1 | 9/1977 |

(Continued)

*Primary Examiner* — Jessica Stultz
*Assistant Examiner* — Sean Hagan

(57) ABSTRACT

The invention relates to a skin treatment device, a lamp for use in such a skin treatment device, and its use. The skin treatment device according to the invention uses a combination of tanning-effective and/or anti-acne effective amounts of blue light in the spectral range from 400-440 nm in addition to the UV-light known in the art. An important advantage is that a lower UV dose can be used, leading to lower health risks, while the exposure times can be kept within acceptable limits, without compromising the skin treatment result.

5 Claims, 2 Drawing Sheets

(56) References Cited

U.S. PATENT DOCUMENTS

2006/0271132 A1* 11/2006 Fiset .............................. 607/94
2007/0060985 A1* 3/2007 Juestel et al. .................. 607/94

FOREIGN PATENT DOCUMENTS

WO   2004098709 A1   11/2004
WO   2007016634 A2   2/2007

* cited by examiner

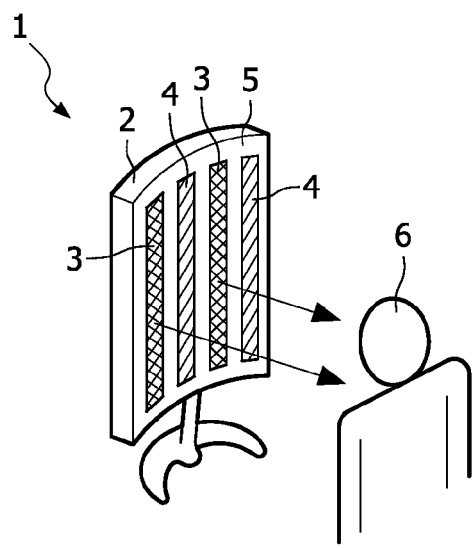
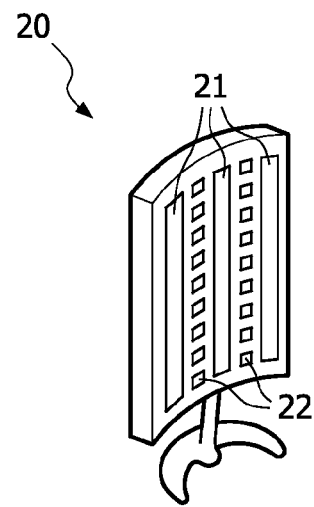
FIG. 1a  FIG. 1b
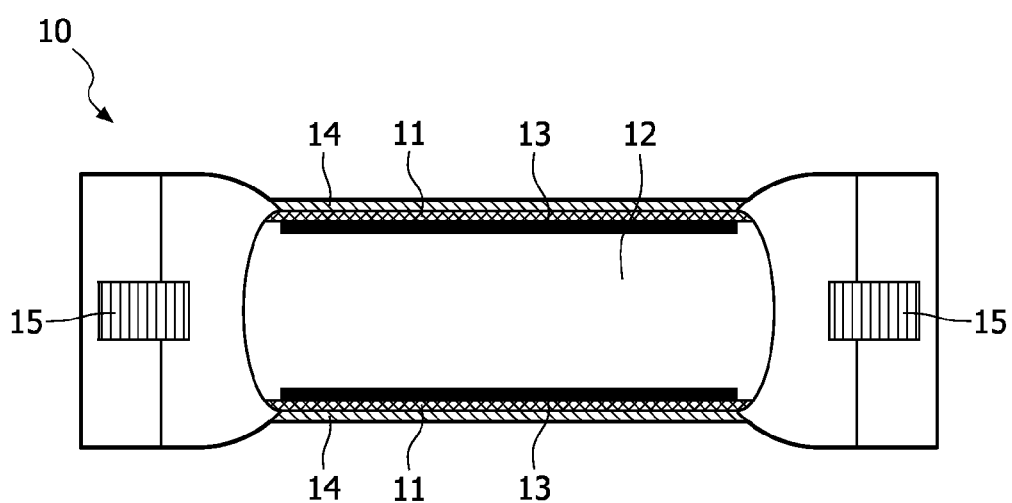
FIG. 2

SKIN TREATMENT DEVICE, LAMP AND USE

FIELD OF THE INVENTION

The invention relates to a skin treatment device, a lamp for use in such a skin treatment device, and its use.

BACKGROUND OF THE INVENTION

In recent years it has become apparent that treatment of the skin of humans for tanning and/or against acne and/or against psoriasis by using skin treatment devices generating UV light has harmful effects to health, such as skin ageing and skin cancer. In particular, skin cancer is a risk at any age, especially for persons under 18 years old, whose immune system is not completely developed yet, and persons above 25 years old who are prone to increased skin ageing (photoageing), all believed to be induced by overexposure to UV radiation. Hence, from a health point of view it is advisable to limit the exposure to UV light. One way to do this is to limit the exposure time, the second way is to lower the intensity of the UV radiation used. Since a long time regulations have limited the maximum erythemal weighted irradiance allowable for professional skin treatment devices, in particular for tanning, to 0.6 W/m$^2$ for both UV-A (320-400 nm) and UV-B (260-320 nm) which was believed to be a level that involves an acceptable health risk. Erythemal weighted irradiance is the power density of UV-A or UV-B light correlated by the sensitivity of the skin at the specific wave lengths, described in DIN 5031-10. Tanning result is a function of the UV-dose, which is determined by the used UV intensities, the exposure time for a tanning session, and the number of tanning sessions. Health risk can be lowered by using a lower UV dose; however this leads to longer exposure times needed to achieve a comparable tanning result, and a longer exposure time also leads to a higher health risk due to a relatively high cumulative UV dose.

It is an object of the invention to enable a skin treatment device that operates at UV levels that pose a more acceptable health risk. In addition it is an object of the invention to enable a skin treatment device achieving a predetermined grade of skin tanning comparable to known tanning devices using comparable exposure times.

SUMMARY OF THE INVENTION

The invention provides a skin treatment device comprising radiation-emitting means suitable for emitting a tanning-effective and/or anti-acne effective amount of UV-light and a tanning-effective and/or anti-acne effective amount of blue light in the spectral range from 400 to 440 nm. Surprisingly, it was found that when tanning-effective amounts of blue light in the range from 400-440 nm are used in addition to UV light regularly used in skin treatment devices, the time to achieve a comparable tanning result is reduced. As a result, the invention also enables the use of a lower UV intensity than regular skin treatment lamps in combination with additional blue light, to yield a comparable tanning and/or anti-acne result in approximately the same exposure time. It is noted that known UV tanning lamps do emit some visible blue light (as can be seen for instance from the spectrum shown in FIG. 3 of U.S. Pat. No. 4,524,299). However, the intensity of the blue light emitted as a side-effect in known UV tanning lights is too low to be tanning-effective. Exposure to lower amounts of UV light dramatically reduces the health risks of skin tanning, anti-acne treatment and anti-psoriasis treatment, such as ageing of the skin and skin cancer. The radiation-emitting means includes a radiation source or multiple radiation sources that emit the desired UV-light and blue light of sufficient intensity, and may include various filters, for instance radiation filters that cut off or reduce the intensity of the radiation at specific harmful wavelengths. Preferred irradiation sources are lamps emitting light of the desired wavelengths. Typically, multiple lamps are used, as well as known optical techniques such as reflectors that help to deliver the radiation in a controlled way to the skin of the user. Examples are for instance known from U.S. Pat. No. 4,524,299 and are included by reference. Tanning-effective amounts depend on the type of skin of the person subjected to the tanning device. UV-light within the region from 190-260 nm is typically undesirable from a health point of view, and therefore preferably blocked by a filter. The range from 260-400 nm is preferred for skin treatment by UV light, giving a good tanning with acceptable health risks, as long as the exposure times and the radiation dose are kept within reasonable limits, preferably between 10-30 minutes per skin treatment session and a dose lower than the erythemal dose (250-400 Jm$^{-2}$ depending on the skin type). Blue light with a wavelength from 400-440 nm is useful for skin treatment, whereas blue light with a wavelength longer than 440 nm yields virtually no tanning and/or anti-acne effect. As blue light from 400-440 nm is less effective in tanning the skin than UV-light, it is preferred if the intensity of the emitted blue light in the range from 400-440 nm as measured in power density (W/m$^2$) is higher than the intensity of the UV-light in the range from 260-400 nm.

It is preferred if the radiation-emitting means are adapted to emit UV-light with a maximum erythemal weighted irradiance of no more than 0.3 W/m$^2$ for both UV-A (320-400 nm) and UV-B (260-320 nm). Health risks are greatly reduced at these intensities. Known skin treatment lamps using only UV light often have an intensity of approximately 0.6 W/m$^2$ for both UV-A (320-400 nm) and UV-B (260-320 nm). The maximum erythemal weighted irradiance is determined using the procedure according to the standard DIN 5031-10, which is included by reference, wherein procedures for measuring power densities for UV-A (320-400 nm) and UV-B (260-320 nm) are described, as well as the calculation from power densities to erythemal weighted irradiance by correlation of the power intensities with the sensitivity of the skin towards specific UV wavelengths (erythemal curve). The desired intensity may be obtained by adjustment of the power of the used irradiation source and/or the application of irradiation filters that diminish the intensity of selected wavelength ranges.

More preferably, the radiation-emitting means are adapted to emit UV-light with a UV erythemal weighted irradiance between 0.1 and 0.3 W/m$^2$. At these intensities the health risk is greatly reduced, but the exposure time needed for tanning is still acceptable. If the irradiance drops below 0.1 W/m$^2$, the tanning effect drops rapidly and the needed exposure times become unacceptably long.

In a preferred embodiment, the radiation-emitting means are adapted to emit blue light in the spectral range from 400 to 440 nm with a power density of at least 100 W/m$^2$. At such intensities, the blue light offers a significant contribution to the tanning and anti-acne treatment, shortening the needed exposure time for a comparable tanning effect when compared to exposure to UV only. For blue light, no maximal erythemal weighted irradiance are established as blue light does not have an erythemal effect. Increasing the blue light intensity yields a higher tanning contribution. Under 100 W/m² the blue light does not show a significant tanning effect in most skin types.

In a preferred embodiment the radiation-emitting means are adapted to emit blue light in an power density between 200 and 500 W/m², preferably between 200 and 400 W/m² Within this range, a very pronounced improvement of the additional tanning effect caused by the blue light is induced. Above 500 W/m² the intensity of the blue light becomes unpleasant for a person exposed to the light.

In a preferred embodiment the radiation-emitting means comprise at least one blue-emitting light source and at least one UV-emitting light source. This allows to adjust the UV radiation and the blue radiation independently. Hence, a conventional UV-lamp may be used along with a suitable blue lamp. Preferably, multiple lamps of both types are used.

It is advantageous if the radiation-emitting means comprises LED lights, in particular blue-emitting LED lights and/or UV-emitting LED lights. LED (light-emitting diode) lights offer a high durability, and a high energy efficiency. Blue LED-lights are particularly advantageous as they are very efficient. Besides, LED-lights allow for a greater freedom of design for skin treatment devices.

In a preferred embodiment of the skin treatment device the radiation-emitting means further comprise LED lights for generating red light. Red light is in particular effective against the external signs of aging of the skin, like wrinkles, lack of firmness etc. In this way the skin treatment device can be used both for tanning and/or acne treatment as well as anti-aging treatment of the skin.

In another preferred embodiment the radiation-emitting means comprises a lamp capable of emitting both a tanning-effective amount of UV-light and a tanning-effective amount of blue light. This has the advantage that both types of light are delivered along the same irradiation paths, making it easier to obtain a homogeneous tanning and/or anti-acne treatment of the exposed skin when compared to a skin treatment device with separate sources for UV and blue light.

The invention further provides a lamp suitable for use in a skin treatment device according to any of the preceding claims, wherein the lamp comprises a light-emitting material comprising at least one UV-emitting component and at least one blue-emitting component. Such lamp can be used in a skin treatment device to yield the advantages described above. The UV-emitting component and the blue-emitting component may be mixed or may be located at separate locations in the lamp. Preferably, however, the components are mixed in order to yield homogeneous radiation. The light-emitting materials may be mixed with other components, for instance a matrix component for the light-emitting components or a binding component to attach the components to the glass or quartz wall of the lamp. The lamp may be based on any known UV lamp designs, for instance the lamps described in U.S. Pat. No. 4,524,299 which is included by reference. Preferably, UV is radiated at least in the range from 260-400 nm and blue light is emitted at least in the range from 400-440 nm. Light outside these ranges may be cut off using radiation filters.

Preferably, the light-emitting material comprises (FeCo)I$_2$:TlI as the UV-emitting component. This material yields a broad UV radiation in the range of 260-400 nm at a high efficiency, at desirable wavelengths that show very good tanning results.

In a preferred embodiment the light-emitting material comprises at least one blue-emitting component selected from the group consisting of GaI$_3$, AlI$_3$, and InI$_3$. These components offer an excellent blue emission in the range from 400-440 nm at efficiency suitable for tanning.

More preferably the light-emitting material comprises GaI$_3$ and AlI$_3$. The combination of GaI$_3$ and AlI$_3$ gave better tanning results than a comparable amount of each component alone, indicating a synergetic effect which may be due to a better coverage of the range from 400-440 nm.

The invention also provides a light-emitting material comprising at least one UV-emitting component and at least one blue-emitting component. Such composition can be used to prepare a lamp according to the invention. The preferred UV-emitting components and blue-emitting components are described above. Apart from these component the composition may comprise other components such as a matrix component or binder component.

The invention further provides the use of tanning-effective amounts of a UV-light in the spectral range from 260 to 400 nm and blue light in the spectral range from 400 to 440 nm for tanning of the human skin. It is noted that tanning is primarily a cosmetic effect, although the exposure to a combination of UV light and blue light may also have medically beneficial side-effects. The combination of UV-light and blue light according to the invention is particularly effective against acne. The use of tanning-effective radiation in the claimed spectral ranges is in particular of interest for use in professional skin treatment devices that may be applied in tanning centres, spa resorts, beauty farms and the like, or skin treatment devices for private use.

The invention will now be further elucidated by the following examples.

BRIEF DESCRIPTION OF THE DRAWINGS

FIGS. 1a and 1b shows skin treatment devices according to the invention.

FIG. 2 shows a lamp for use in a skin treatment device according to the invention.

DETAILED DESCRIPTION OF EMBODIMENTS

Figure 3:
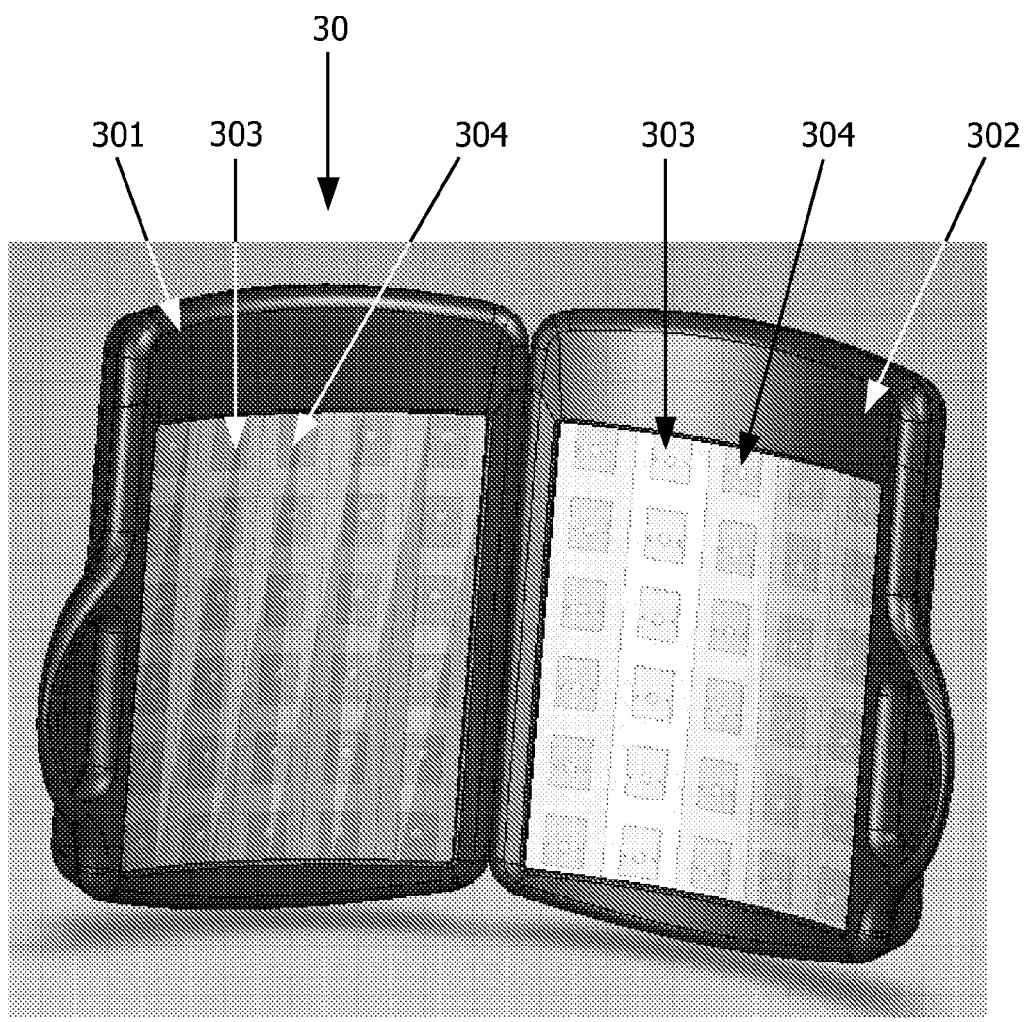
FIG. 3 shows an alternative skin treatment device according to the invention.

FIG. 1a shows a skin treatment device 1, comprising lamp holder 2 that fits a number of known UV-emitting lamps 3 as well as a number of blue-emitting lamps 4, positioned in an alternating fashion. The UV lamps 3 emit primarily in the range from 260-320 nm, whereas the blue lamps 4 primarily emit at wavelengths from 400-440 nm. Undesired UV-light with wavelengths shorter than 260 nm is blocked by a suitable UV filter integrated in the lamps or the device. The curved reflector 5 behind the lamps 3, 4 directs the combined blue and UV light from the lamps 3,4 towards the user 6, inducing a desirable tanning and/or anti-acne treatment of the user's skin after a repeated sessions of 10-30 mins of exposure the lamp during at least 2 days, preferably at least 4 days. In addition, the skin treatment device can be used for anti-psoriasis treatment. The separate blue lamps 4 and UV lamps 3 may be replaced by lamps that emit both UV light and blue light in the wavelength ranges indicated above. The skin treatment device 1 shown here is relatively small, but the same technology according to the invention may be applied in larger skin treatment devices known in the art.

FIG. 1b shows another preferred embodiment of a skin treatment device 20 according to the invention, comparable to the device of FIG. 1a. In this case, the skin treatment device is provided with conventional UV-only lamps 21 emitting UV-A and UV-B, as well as arrays of blue LEDs 22 emitting blue light in the range from 400-440 nm. Compared to the device of FIG. 1a, this device is more energy-efficient, as well as being more compact.

In a preferred embodiment of a skin treatment device 20 according to the invention, the device further comprises LEDs emitting red light in the range of 600-660 nm, not shown in FIG. 1b. The red light is beneficial against the signs of skin aging. In this way the effect of the skin treatment device is two-fold: tanning and/or anti-acne treatment as well as anti-aging treatment.

In another preferred embodiment of a skin treatment device according to the invention the LEDs are so-called high power LEDs, i.e. LEDs delivering a light output of typically 600 mW at 700 mA. These type of LEDs provide sufficient blue, UV and/or red light to treat the whole face or other part of the human body in relatively short amount of time with a limited amount of LEDs.

FIG. 2 shows a high intensity discharge (HID) lamp 10 capable of emitting both UV light and blue light for use in a skin treatment device according to the invention, for example the device 1 in FIG. 1. The lamp according to the invention has a cylindrical glass vessel 11 with a volume of 8 cm$^3$. Preferably, the glass has a good transparency in the relevant range of the spectrum: UV-A, UV-B (260-400 nm) and the blue range from 400-440 nm. The inner volume 12 is filled with 80 mbar of argon and/or krypton and 20 mg of mercury. In addition, the inner volume 12 comprises 2.5 mg (FeCo)I$_2$:TlI as the UV-emitting component, and 1 mg of GaI$_3$=1 mg as the blue-emitting component, optionally supplied with 0.5 mg AgI$_3$ as a secondary blue-emitting component. In a preferred embodiment the inner volume comprises GaI$_3$ and AlI$_3$ as the blue-emitting component. The amounts of the components may be varied, and the optimum composition depends on geometric parameters of the lamp such as length and diameter as well as the voltage that is to be applied to the electrodes 15 of the lamp 10. Optionally, a UV-filter 14 may be integrated in the lamp lowering the UV-output to acceptable levels. In particular the wavelengths shorter than 260 nm pose a health risk and will need to be blocked from the users skin. The UV-filter may also be placed externally between a user and the lamp 10. The volume and shape of the lamp according to the invention may be adjusted to fit specific skin treatment devices. In particular lamps geometries known from UV-only lamps used for skin treatment purposes may be modified according to the invention. In an alternative embodiment, the lamp 10 further comprises a layer 13 for generation of the UV radiation. The layer 13 comprises one or more materials selected from the group consisting of BaSi2O5:Pb, SrB4O7:Eu, LaPO4:Ce, SrCe0.8MgAl11O18, GdB3O6:Bi, LaB3O6:Bi, YPO$_4$:Ce, and GdPO4:Ce.

FIG. 3 shows another preferred embodiment of a skin treatment device 30 according to the invention, comprising two lamp holders 301, 302 both fitting a number of known UV-emitting LEDs 303 as well as a number of blue-emitting LEDs 304, positioned in arrays in an alternating fashion. The lamp holders 301, 302 are connected to each other via a hinge, not shown, allowing to fold-up both holders. The skin treatment device 30 may further have two metallic legs, not shown in FIG. 3, for positioning the skin treatment device 30 in a vertical or horizontal position. In another preferred embodiment of a skin treatment device 30 according to the invention, the device comprises only arrays of blue-emitting LEDs 304. The blue LEDs 304 have a peak emission at 430 nm and also generate a small amount of radiation in the UV range.

Comparative Tests

Experiments were performed, comparing the intensities and exposure times needed to yield a certain tanning result. This was performed by exposing different parts of the skin of test persons at different intensities with an exposure time of 15 minutes during 4 subsequent days, and comparing the skin tans obtained under different circumstances. The results are summarized in table I. UV-A (320-400 nm) and UV-B (260-320 nm) intensities are given as maximal erythemal weighted irradiance values according to DIN 5031-10, blue light (400 to 440 nm) is given as an unmodified power density. The tanning results are given as relative scores. The intensities can be adjusted by using separate lamps for UV and blue light, or by using lamps emitting both blue light and UV light wherein the amounts of the UV-emitting components and blue-emitting components are adjusted to give the desired ratio. Another possibility to adjust the amount and ratio of UV and blue light is by using suitable filters placed between the radiation source and the exposed skin of the test person.

TABLE I

| Experiment # | UV-A intensity (W/m$^2$) | UV-B intensity (W/m$^2$) | Blue intensity (W/m$^2$) | Exposure time (min × days) | Tanning result (relative) |
|---|---|---|---|---|---|
| 1 | 0.6 | 0.6 | 0.5* | 15 × 4 | ++ |
| 2 | 0.3 | 0.3 | 0.5* | 15 × 4 | + |
| 3 | 0.3 | 0.3 | 100 | 15 × 4 | +** |
| 4 | 0.3 | 0.3 | 300 | 15 × 4 | ++ |

*at this intensity, blue light has no significant contribution to the tanning effect.
**experiment 3 gives a slightly deeper tan than experiment 2 after 4 days of exposure.

In experiment 1 a regular UV-only lamp is used. Note that such UV-lamps also produce a small amount of blue radiation, that does not contribute significantly to the tanning. After 4 days of 15 minutes of exposure, tanning result is obtained that can be used as a reference to the other experiments, performed on the same test person.

Experiment 2 uses only half of the UV intensities of experiment 1, and shows significantly less tanning after 4 days than experiment 1.

Experiment 3 uses the same reduced UV intensities with an amount of blue light added. At a power density of 100 W/m$^2$, a minor but significant improvement in tanning result was noted.

In experiment 4, the relatively low UV intensities of experiment 2 were combined with a relatively high intensity of blue light. A major improvement in tanning was noted when compared to experiment 3, showing that a higher amount of blue light leads to improved tanning effect. At the used power density of 300 W/m$^2$ in the blue spectrum from 400-440 nm, the final tanning result was comparable with a regular UV-only lamp.

The invention claimed is:

1. Lamp suitable for use in a skin treatment device comprising radiation-emitting means, said means comprising a light-emitting material capable of emitting a tanning-effective and/or anti-acne effective amount of UV-light and a tanning-effective and/or anti-acne effective amount of blue light;
   wherein the lamp is adapted to emit UV-light with a erythemal weighted irradiance between 0.1 and 0.3 W/m$^2$ for both UV-A (320-400 nm) and UV-B (260-320 nm), and wherein the lamp is adapted to emit blue light in the spectral range from 400 to 440 TIM with a power density between 200 and 500 W/m$^2$;

wherein the light-emitting material comprises at least one UV-emitting component and at least one blue-emitting component; and, wherein the light-emitting material comprises (FeCo)I$_2$TlI as the UV-emitting component.

2. Skin treatment device according to, claim 1, wherein the radiation-emitting means comprises a lamp which comprises a light-emitting material capable of emitting both a tanning-effective and/or anti-acne effective amount of UV-light and a tanning-effective and/or anti-acne effective amount of blue light.

3. Skin treatment device according to claim 1, wherein the radiation-emitting means further comprise LEI) lights for generating red light.

4. Lamp according to claim 1 wherein the light-emitting material comprises at least one component selected from the group consisting of: GaI$_3$, AlI$_3$ and InI$_3$ as the blue-emitting component.

5. Lamp according to claim 4, wherein the light-emitting material comprises GaI$_3$ and AlI$_3$.

* * * * *